(12) United States Patent
Weber

(10) Patent No.: US 10,307,112 B2
(45) Date of Patent: Jun. 4, 2019

(54) FROSTBITE WARNING SYSTEM

(71) Applicant: Allie Weber, Sioux Falls, SD (US)

(72) Inventor: Allie Weber, Sioux Falls, SD (US)

(*) Notice: Subject to any disclaimer, the term of this patent is extended or adjusted under 35 U.S.C. 154(b) by 0 days.

(21) Appl. No.: 15/910,613

(22) Filed: Mar. 2, 2018

(65) Prior Publication Data

US 2018/0249969 A1 Sep. 6, 2018

Related U.S. Application Data

(60) Provisional application No. 62/466,237, filed on Mar. 2, 2017.

(51) Int. Cl.
| | |
|---|---|
| *A61B 5/00* | (2006.01) |
| *A61B 5/01* | (2006.01) |
| *G08B 21/02* | (2006.01) |
| *G08B 21/04* | (2006.01) |
| *G08B 21/18* | (2006.01) |

(52) U.S. Cl.
CPC .............. *A61B 5/746* (2013.01); *A61B 5/01* (2013.01); *A61B 5/6803* (2013.01); *A61B 5/6806* (2013.01); *A61B 5/6807* (2013.01); *A61B 5/7405* (2013.01); *G08B 21/02* (2013.01); *G08B 21/0453* (2013.01); *G08B 21/182* (2013.01); *A61B 2503/06* (2013.01); *A61B 2560/0242* (2013.01)

(58) Field of Classification Search
CPC ......... A61B 5/746; A61B 5/01; A61B 5/6803; A61B 5/6806; A61B 5/6807; A61B 5/7405; A61B 2503/06; A61B 2560/0242; G08B 21/02; G08B 21/182
See application file for complete search history.

(56) References Cited

U.S. PATENT DOCUMENTS

| | | | | |
|---|---|---|---|---|
| 5,796,345 | A * | 8/1998 | Leventis | A61F 13/42 340/604 |
| 6,198,394 | B1 * | 3/2001 | Jacobsen | A61B 5/1112 340/573.1 |
| 6,559,828 | B1 * | 5/2003 | Impio | G06F 1/1615 345/156 |
| 9,082,025 | B2 * | 7/2015 | Fastert | G06K 19/027 |
| 9,846,829 | B2 * | 12/2017 | Fastert | G06K 19/027 |
| 2006/0252999 | A1 * | 11/2006 | Devaul | A61B 5/0024 600/300 |
| 2009/0046760 | A1 * | 2/2009 | Matheson | A41D 13/005 374/141 |

(Continued)

*Primary Examiner* — Joseph H Feild
*Assistant Examiner* — Rufus C Point
(74) *Attorney, Agent, or Firm* — Nelson Mullins Riley & Scarborough LLP

(57) ABSTRACT

A frostbite warning system for monitoring conditions adjacent a portion of a user, including an article of clothing that is configured to be disposed on the portion of the user's body, a temperature sensor that is configured to detect a temperature within the article of clothing and produce a first input signal that is indicative of the temperature within the article of clothing, a processor configured to receive the first input signal, compare the temperature in the article of clothing to a threshold temperature at which a first warning signal is produced, and produce the first warning signal when the temperature within the article of clothing is equal to or less than the threshold temperature.

5 Claims, 3 Drawing Sheets

(56) References Cited

U.S. PATENT DOCUMENTS

| | | | |
|---|---|---|---|
| 2009/0204100 A1* | 8/2009 | Van Pieterson | A61B 5/0008 604/503 |
| 2013/0271602 A1* | 10/2013 | Bentley | H04N 7/18 348/143 |
| 2014/0097944 A1* | 4/2014 | Fastert | G06K 19/027 340/10.51 |
| 2014/0340218 A1* | 11/2014 | Sutherland | G08B 21/043 340/539.12 |
| 2015/0083705 A1* | 3/2015 | Cronn | H05B 3/347 219/211 |
| 2015/0094914 A1* | 4/2015 | Abreu | B60H 1/00742 701/41 |
| 2015/0286913 A1* | 10/2015 | Fastert | G06K 19/027 374/163 |
| 2016/0120691 A1* | 5/2016 | Kirwan | A61F 7/02 607/111 |

\* cited by examiner

FROSTBITE WARNING SYSTEM

CLAIM OF PRIORITY

This application claims the benefit of U.S. Provisional Application No. 62/466,237 filed Mar. 2, 2017, the disclosure which is hereby incorporated by reference in its entirety into the specification of this application.

FIELD OF THE INVENTION

The present invention relates generally to temperature monitoring and warning systems. More particularly, the present invention relates to systems to assist a user in avoiding possible frostbite.

BACKGROUND OF THE INVENTION

Frostbite occurs when the water within a person's tissue begins to crystalize, thereby damaging the tissue even after the conditions causing the frostbite no longer exist and the crystals melt. There are varying levels of frostbite that are dependent upon the extent to which the water within the tissue crystalizes. For example, in minor frostbite instances a person may experience only slight discoloration, such as reddening of the affected area, and minor tingling, whereas in severe instances of frostbite a person may lose portions of their extremities, such as fingers and toes, and may even lose entire limbs. As would be expected, instances of frostbite typically occur in environments in which a person is exposed to extremely cold temperatures, such as, but not limited to, outdoor activities during winter, walk-in freezers, etc. Note, however, frostbite may occur in environments that one would not typically expect due to extenuating circumstances.

For example, the potential for frostbite in more moderate environments is increased when protective clothing becomes wet, such as by contact with liquids, perspiration of the person wearing the clothing, etc. Moreover, once the protective clothing is wetted, contact of that clothing with items that may be colder than the ambient air environment, such as ice, metal objects, etc., can enhance the speed with which frostbite sets in. As well, various groups of people may be more prone to experiencing frostbite than the general population. For example, people having reduced circulation in their extremities due to old age, diabetes, other circulatory issues, and children tend to experience the on-set of frostbite earlier than the general population. For children, the potential to be distracted by activities such as sledding, playing, etc., as well as a possible general lack of knowledge as to the warning signs of frostbite make them a particularly at risk group. Moreover, the fact that a first instance of frostbite makes that person more prone to a second instance of frostbite in the same region means it is very desirable to avoid all instances if possible.

A number of methodologies exist that can be utilized in an effort to avoid instances of frostbite. For example, it is known to use protective gear, such as gloves, hats, socks, etc., that prevent the intrusion of water into the garment yet allow for perspiration to be evaporated through the material of the garment. However, these garments can be very expensive and are not necessarily 100% effective at keeping the user and the garment dry. Chemical warming packs may also be placed in various garments such as gloves, boots, etc. However, chemical warming packs can be expensive and create wasteful by-products that must be disposed of. Glove driers, anti-perspirants, and talcum powders may be used to help alleviate issues related to dampened articles of clothing, but provide no indication to the person wearing those articles as to whether or not potential conditions for frostbite exist.

Therefore, it is desirable that improved systems and methodologies be developed to assist people in preventing frostbite and the medical issues that can be associated therewith. The present invention recognizes and addresses considerations of prior art constructions and methods.

SUMMARY OF THE INVENTION

One embodiment of the present invention provides a frostbite warning system for monitoring conditions adjacent a portion of a user, including an article of clothing that is configured to be disposed on the portion of the user's body, a temperature sensor that is configured to detect a temperature within the article of clothing adjacent the portion of the user's body that is disposed within the article of clothing and produce a first input signal that is indicative of the temperature within the article of clothing, a processor configured to receive the first input signal, compare the temperature in the article of clothing to a threshold temperature at which a first warning signal is produced, and produce the first warning signal when the temperature within the article of clothing is equal to or less than the threshold temperature.

Another embodiment of the present invention provides a method of providing a warning to an individual in accordance with a temperature adjacent a portion of the individual, including the steps of providing an article of clothing, placing the article of clothing on the portion of the individual, providing a temperature sensor that is disposed within the article of clothing adjacent the portion of the individual, producing a first input signal that is indicative of the temperature within the article of clothing adjacent the portion of the individual, and providing an audible indication when the temperature within the article of clothing is less than or equal to a threshold temperature.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
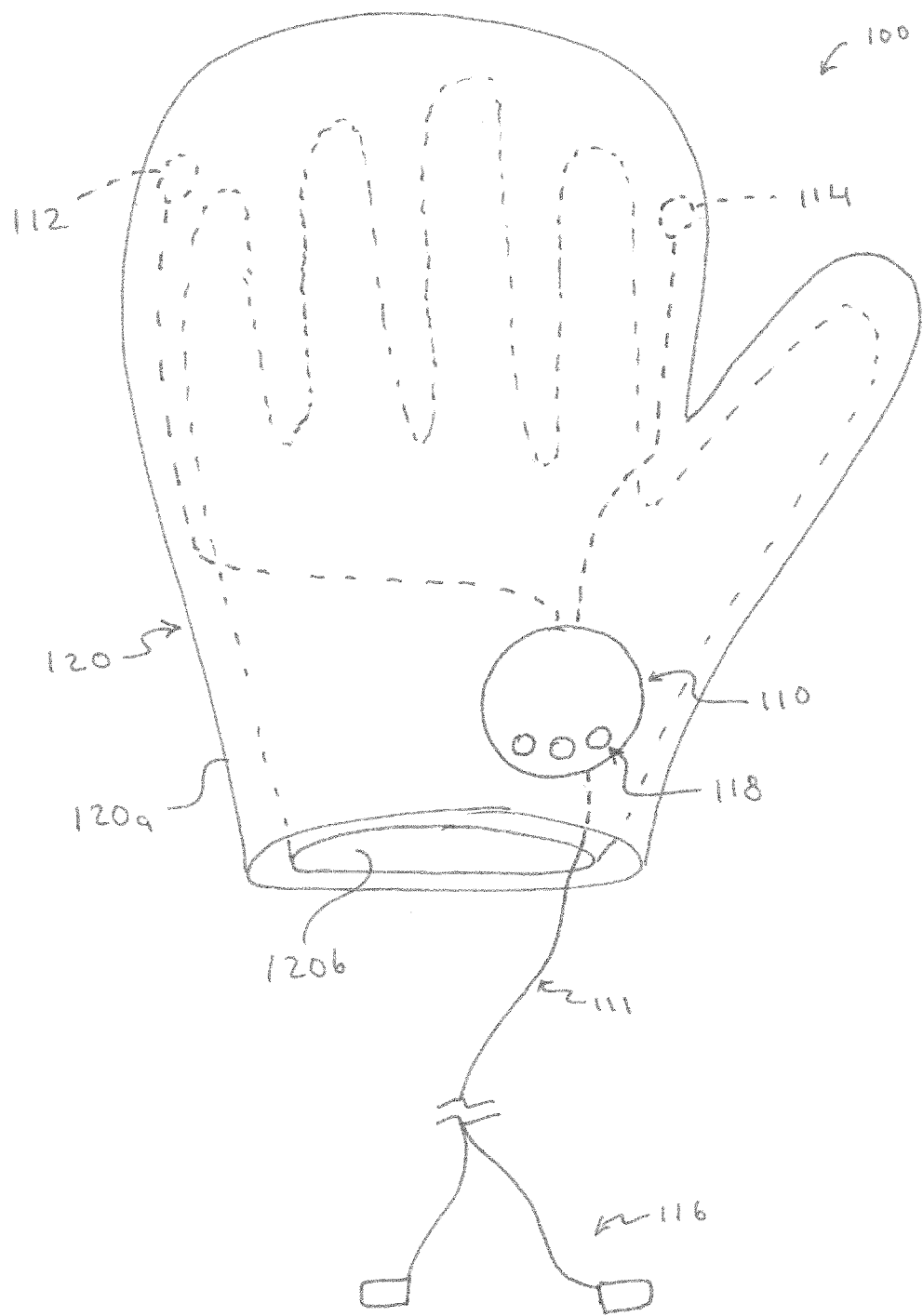
FIG. 1 is a schematic view of a frostbite warning system in accordance with an embodiment of the present invention.

Repeat use of reference characters in the present specification and drawings is intended to represent same or analogous features or elements of the invention according to the disclosure.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

As shown in FIG. 1, a frostbite warning system 100 in accordance with an embodiment of the present invention is shown. The frostbite warning system 100 preferably includes a programmable logic controller 110, a temperature sensor 112, a moisture sensor 114, an audible indicator 116, and a visual indicator 118 that are all associated with a corresponding article of clothing 120. As shown, the article of clothing 120 is a mitten including an outer mitten portion 120a and an inner liner portion 120b in which a user inserts his hand. Note, in alternative embodiments, the frostbite warning system 100 may be used with gloves, mittens, socks, hats, etc., that do not include an inner liner portion.

Still referring to FIG. 1, the programmable logic controller 110 is disposed directly on the outer mitten portion 120a and includes a series of wires 111 that connect the programmable logic controller 110 to the corresponding temperature sensor 112 and moisture sensor 114. A clear protective coating may be provided to protect the programmable logic controller 110. In the preferred embodiment shown, the programmable logic controller 110 is a LilyPad Arduino Uno. As shown, the temperature sensor 112 and moisture sensor 114 are disposed between the outer mitten portion 120a and the inner liner portion 110b adjacent the distal ends of the user's fingers, i.e., at the tips of the finger sleeves of the inner sleeve portion 120b. This positioning is preferential as the onset of frostbite tends to occur at the most distal portions of a person's extremities, such as the fingers and toes. As shown, the visual indicators 118 are preferably light emitting diodes (LEDs) and the audible indicator 116 is a pair of earbuds. Note, however, an external speaker, headphones, etc., may be utilized as well to provide an audible indication when the potential conditions for frostbite occur.

In use, a user selects a threshold temperature at which the frostbite warning system 100 is to provide a visual and/or audible indication when that temperature is reached. The threshold temperature may be selected based upon a number of factors that will vary for each individual user. For example, a higher threshold temperature maybe selected for a user that is either elderly, suffers from a circulatory disorder, is very young, has experienced frostbite previously, etc., as these groups may be more prone to experience frostbite at temperatures that are higher than would be expected for the general population. Similarly, the moisture sensor 114 maybe selected based upon an acceptable moisture level within the article of clothing for a given user. Once a user places his hand in the mitten 120, the programmable logic controller 110 will receive electrical inputs from the temperature sensor 112 and the moisture sensor 114 dependent upon the conditions within the article of clothing 120. If the temperature within the article of clothing 120 goes low enough to reach the threshold temperature, an input signal for the temperature sensor 112 is received by the programmable logic controller 110 that in turn provides an audible warning signal to the user via the earbuds 116 and a visual warning via the LEDs 118. As such, the user is now aware that the potential conditions exist for the onset of frostbite and may seek to remedy those conditions.

Figure 2:
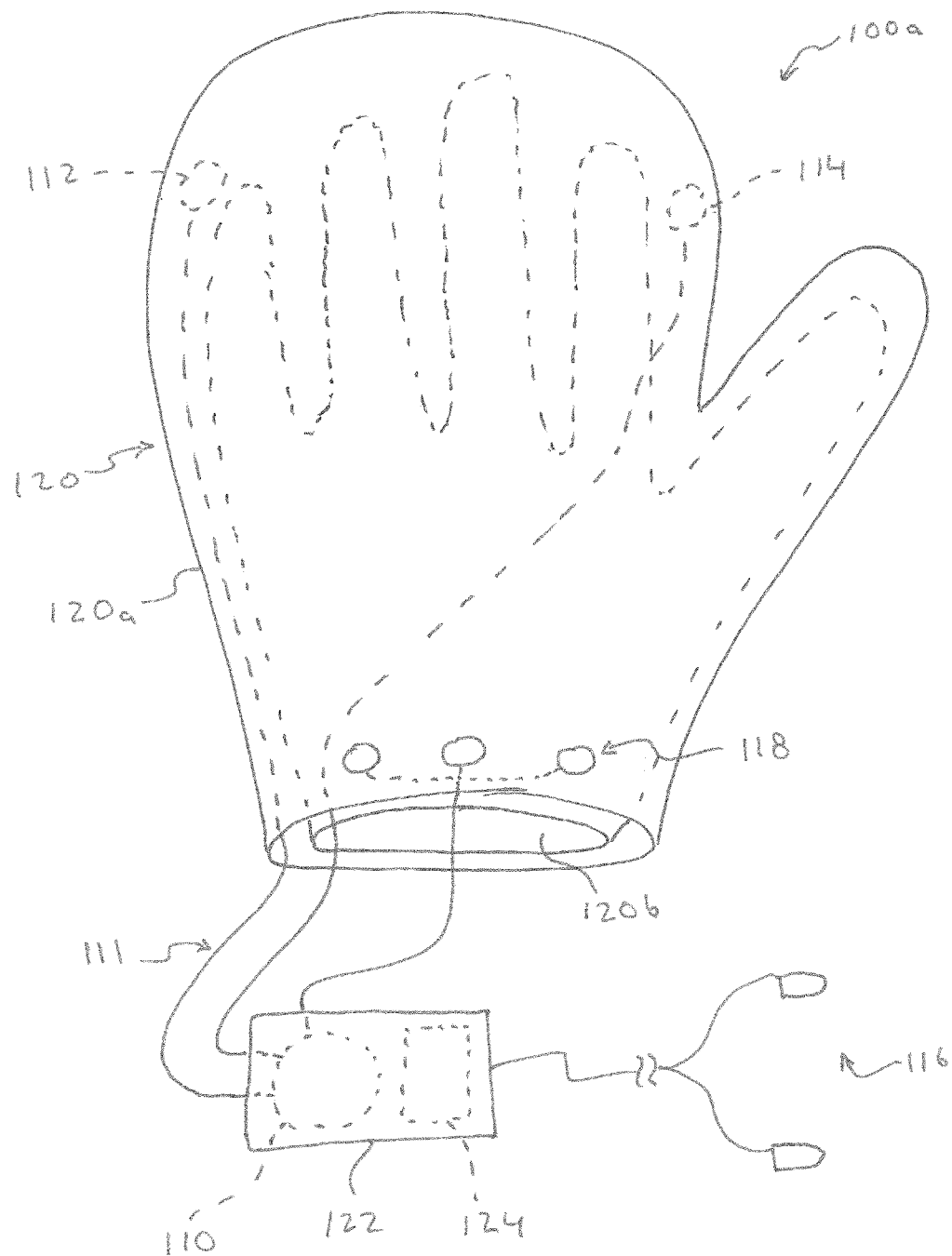
FIG. 2 is a schematic view of an alternate embodiment of a frostbite warning system in accordance with an alternate embodiment of the present invention.
Figure 3:
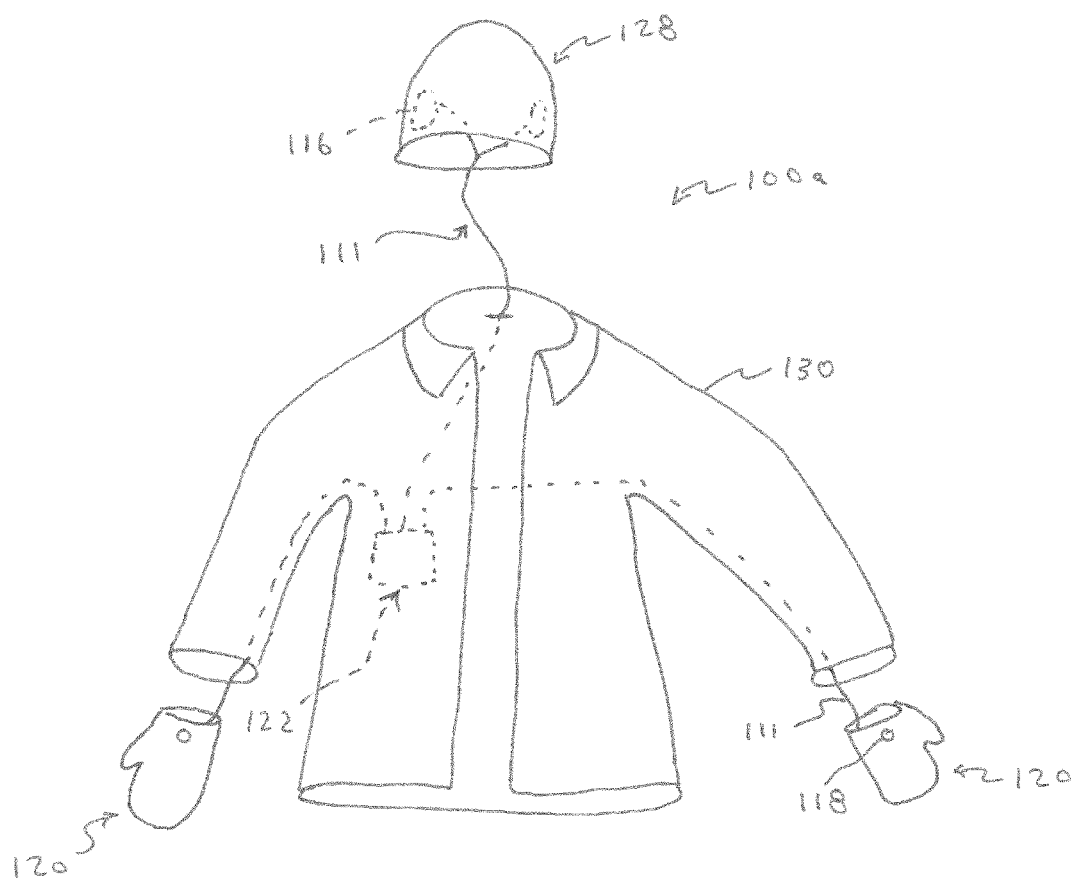
FIG. 3 is a schematic view of the frostbite warning system as shown in FIG. 2 included in a coat of a user.

Referring now to FIG. 2, an alternate embodiment of a frostbite warning system 100a in accordance with the present invention as shown. The frostbite warning system 100a differs primarily from the frostbite warning system 100 shown in FIG. 1 in that the programmable logic controller 110 and corresponding battery 124 are housed in a case 122 that is external to the article of clothing 120 that is being monitored. This allows the programmable logic controller 110 to be stored in a place, such as an inner pocket of the user's coat 130, as shown in FIG. 3, where it is less likely to become damaged. As well, the case 122 is preferably water-tight to help protect the programmable logic controller 110 and associated wiring. Note, a visual indicator 118, in the present case LEDs, are still preferably positioned on an external surface of the article of clothing 120 that is being monitored. As such, the user will still be able to see the visual warning of potential frostbite conditions.

Referring additionally to FIG. 3, in a preferred embodiment of the frostbite warning system 100a, both of the user's mittens 120 are monitored, with the wires 111 connecting the mittens 120 to the programmable logic controller 110 running through the liner of the user's coat 130. As well, the audible indicator 116, in the instant case headphones, are incorporated into the user's hat 128 so that each headphone is positioned adjacent to the corresponding ear of the user when hat 128 is being worn. This configuration may be prove especially desirable when the frostbite warning system 100a is utilized by young children as it insures proper placement of the audible indicator 116. Note, the placement of the temperature sensors 112 and moisture sensors 114 in the discussed embodiments serve only as example placements. Additional sensors may be incorporated in the hat 128 adjacent the user's ears, in the user's socks (not shown), etc.

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

What is claimed is:

1. A frostbite warning system for monitoring conditions adjacent a portion of a user, comprising:
    an article of clothing that is configured to be disposed on the portion of the user's body; a temperature sensor that is configured to detect a temperature within the article of clothing adjacent the portion of the user's body that is disposed within the article of clothing and produce a first input signal that is indicative of the temperature within the article of clothing;
    a programmable logic controller configured to receive the first input signal, compare the temperature in the article of clothing to a threshold temperature at which a first warning signal is produced, and produce the first warning signal when the temperature within the article of clothing is equal to or less than the threshold temperature;
    an audible indicator, wherein the first warning signal from the programmable logic controller causes the audible indicator to provide an audible indication to the user and the audible indicator is one of a pair of ear buds, a pair of headphones, and a speaker; and
    a moisture sensor that is configured to detect a moisture level within the article of clothing adjacent the portion of the user's body that is disposed in the article of clothing and produce a second input signal that is indicative of the moisture level within the article of clothing, wherein the programmable logic controller is further configured to receive the second input signal compare the moisture level in the article of clothing to a threshold moisture level at which a second warning signal is produced, and produce the second warning signal when the moisture level within the article of clothing equals or exceeds the threshold moisture level.

2. The frostbite warning system of claim 1, wherein the second warning signal from the programmable logic controller causes the audible indicator to provide an audible indication to the user.

3. The frostbite warning system of claim 2, further comprising a visual indicator, wherein the first warning signal and the second warning signal from the programmable logic controller causes the visual indicator to provide a visual indication to the user.

4. The frostbite warning system of claim 3, wherein the visual indicator is one or more light emitting diodes.

5. The frostbite warning system of claim 1, wherein the article of clothing is one of a mitten, a glove, a sock, and a hat.

* * * * *